United States Patent [19]

Noesberger et al.

[11] Patent Number: 4,963,153
[45] Date of Patent: Oct. 16, 1990

[54] METAL TIBIAL ANCHORING PART FOR A PARTIAL KNEE JOINT PROSTHESIS

[75] Inventors: Bruno Noesberger, Interlaken; Otto Frey, Winterthur, both of Switzerland

[73] Assignees: Sulzer Brothers Limited, Winterthur; Protek AG, Berne, both of Switzerland

[21] Appl. No.: 205,466

[22] Filed: Jun. 10, 1988

[30] Foreign Application Priority Data

Jun. 30, 1987 [CH] Switzerland ............... 2462/87

[51] Int. Cl.$^5$ ............................................. A61F 2/38
[52] U.S. Cl. ....................................................... 623/20
[58] Field of Search ........................................ 623/20

[56] References Cited

U.S. PATENT DOCUMENTS 3,715,763  2/1973  Link ........................... 623/20
3,869,731  3/1975  Waugh et al. ............. 623/20

FOREIGN PATENT DOCUMENTS 1390494  4/1975  United Kingdom .

OTHER PUBLICATIONS

Zimmer Product Description, Journal of Bone and Joint Surgery, vol. 52-A, No. 3, Apr., 1970.

Primary Examiner—Randall L. Green
Assistant Examiner—Stephanie L. Iantorno
Attorney, Agent, or Firm—Kenyon & Kenyon

[57] ABSTRACT

The tibial anchoring part is formed of a flat semi-circular bearing element which defines a tibia plateau for receiving a plastic bearing element as well as a blade-like fixing element. This fixing element extends at an incline from ventral to dorsal in a distal direction and has a cutting edge at the dorsal edge for penetrating into the bone. An enlargement is also provided distally of the fixing element to prevent inadvertent pullout of the part and is also provided with a cutting edge at the dorsal edge of the anchoring part.

20 Claims, 1 Drawing Sheet

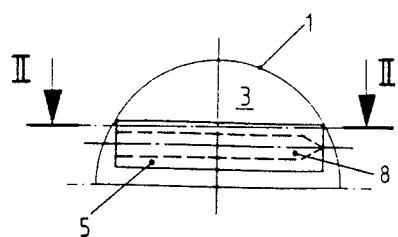
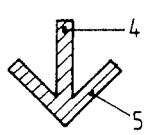
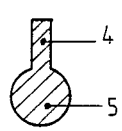
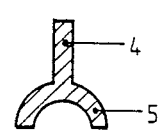
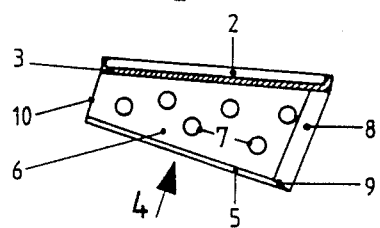
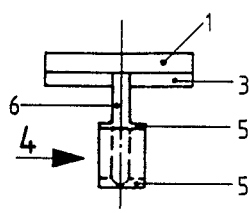
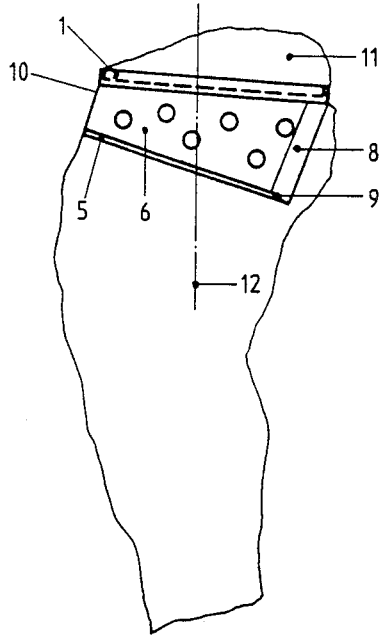
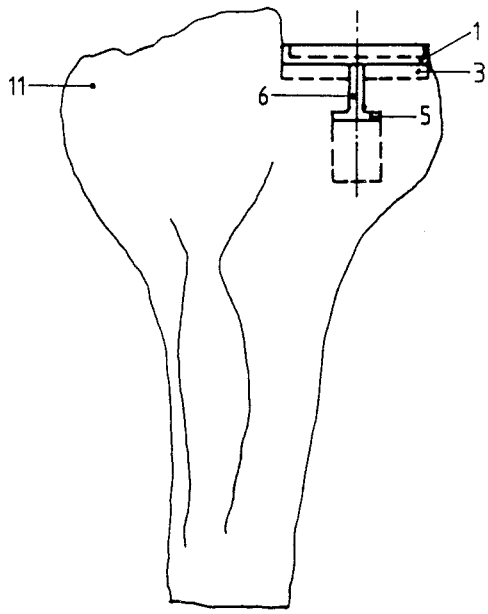

METAL TIBIAL ANCHORING PART FOR A PARTIAL KNEE JOINT PROSTHESIS

This invention relates to a metal tibial anchoring part for a partial knee joint prosthesis More particularly, this invention relates to a tibial anchoring part for cementless anchoring in a tibia.

Heretofore, the cementless anchorage of tibia parts in a tibia has usually been accomplished by means of pins or nails, for example as described in European Patent Application No. 151,724 and European Patent Application No. 170,779. Generally, the pins or nails have been introduced into bores in the tibia head which extend in the direction of the longitudinal axis of the tibia into the bone.

With natural joints where destruction has been minor and where the ligaments, such as the lateral and crucial ligaments, are still sound and functional, difficulties arise in the surgical anchorage of tibia parts having pins or nails because the ligament arrangement prevents the femur and tibia from displacing from each other and being "held apart" in the direction of the longitudinal axis by other than a relatively slight amount. Accordingly, it has been difficult to make the bores in the tibia head which are necessary for anchorage if the ligament arrangement is not to be disturbed during the surgical operation.

U.S. Pat. No. 3,869,731 describes an articulated two-part prosthesis wherein a C-shaped flat disk tibial component is provided with curved rings on the bottom and is adapted to be connected to and rest on a proximal plateau surface of the tibia after preparation. However, a reliable securement of this type of component cannot be ensured in a cementless anchorage.

French Patent No. 2,550,936 describes the use of various inserts for the repair of a knee joint while British Patent No. 1,390,494 describes a femoral implant. However, neither describes a tibial anchoring part which can be readily put in place to provide a plateau for receiving a plastic bearing element for a femur condyle.

Accordingly, it is an object of the invention to provide a tibial anchoring part for cementless anchoring in a tibia.

It is another object of the invention to provide a tibial component which can be mounted in a tibia without a need to interfere with the ligament arrangement of a knee joint.

Briefly, the invention provides a metal tibial anchoring part for a partial knee joint prosthesis which is comprised of a flat semi-circular bearing element and a fixing element secured to and extending from the bearing element. The bearing element defines a tibia plateau for receiving a plastic bearing element for a femur condyle. The fixing element slopes in a downward direction from ventral to dorsal in a distal direction and has a cutting edge along a dorsal front edge for penetrating into a tibia.

The anchoring part can be driven into a tibia head from ventral to dorsal after a damaged medial or lateral condyle has been removed. The cut surface of the cleared condyle of the natural tibia head then forms the bearing surface for the tibia plateau of the anchoring part.

The fixing element which slopes obliquely from ventral to dorsal has a blade-like stem extending perpendicularly from the bearing element and includes an enlargement at the distal end to prevent the anchoring part from sliding out of the bone in the manner of a drawer.

In one embodiment, the stem and enlargement of the fixing element define a T-shaped cross section. In addition, the stem has a pair of side walls defining the cutting edge centrally thereof while the enlargement has a one-sided cutting edge sharpened to distal. The vertical cutting edge of the stem causes a distribution of the displaced bond tissue to both sides of the stem while the one-sided cutting edge of the enlargement serves to compact the displaced spongiosa in a proximal direction in order to further support the adhesion of the anchoring part in the bond. This adhesion can be further improved over the long term by providing openings in the blade-like stem for the ingrowth of bone tissue.

Advantageously, in order to further adapt to the anatomical situation, the vertical edges of the stem are inclined to ventral and/or the bearing element is inclined to distal/dorsal relative to a horizontal plane.

The anchoring part may be made of any of the known metallic prosthesis materials and may be forged or cast. Further, the faces of the part which are to face a bone may be provided with a coating and/or structure as is known.

An artificial tibia condyle, for example, made of polyethylene of the specifications customary for implants, may be used as a sliding and bearing surface opposite a femur prosthesis which is usually made of metal. This artificial tibia condyle may be connected with the anchoring part during manufacture or by means of suitable fasteners during a surgical operation.

These and other objects and advantages of the invention will become more apparent from the following detailed description taken in conjunction with the accompanying drawings wherein FIG. 1 illustrates a plan view of an anchoring part constructed in accordance with the invention;

FIG. 2 illustrates a view taken on line II—II of FIG. 1;

FIG. 3 illustrates a ventral view of the anchoring part;

FIG. 4 illustrates a view of the anchoring part in place in a tibia;

FIG. 5 illustrates a ventral view of a tibia with the anchoring part in place;

FIG. 6 illustrates a modified cross-sectional shape of the fixing element of the anchoring part in accordance with the invention;

FIG. 7 illustrates a further cross-sectional view of a modified enlargement for the fixing element in accordance with the invention;

FIG. 8 illustrates a further modified enlargement for the fixing element in accordance with the invention;

FIG. 9 illustrates a further modified fixing element in accordance with the invention; and FIG. 10 illustrates a view similar to FIG. 9 of a modified fixing element in accordance with the invention.

Referring to FIGS. 1 and 2, the metal tibial anchoring part is constructed for use with a partial knee joint prosthesis. As indicated, the anchoring part has a flat semi-circular bearing element 1 which is provided with a depression, 2 which defines a tibia plateau 3 for receiving a plastic bearing element (not shown) for a femur condyle (not shown). In the anchoring part has a blade-like fixing element 4 extending perpendicularly from the bearing element 1 which is formed of a blade-like stem 6 and an enlargement 5 at a distal end of the stem 6. As illustrated in FIG. 3, the stem 6 and enlargement 5 define a T-shape cross-section.

Referring to FIG. 2, the blade-like stem 6 is provided with a plurality of openings 7 for the ingrowth of bone tissue. In addition, the stem 6 is provided with a pair of side walls at the "front" edge to define a cutting edge 8 which is located centrally of the stem 6. The enlargement which is in the form of a cross beam or a flange has a cutting edge 9 which is one-sided, i.e. sharpened to distal so that spongiosa detached thereby is displaced upwardly, as viewed in FIG. 2.

The front cutting edge 8 and rear edge 10 of the stem 6 are inclined to ventral for adaptation to the anatomical conditions. In addition, the surface area of the stem 6 widens in the ventral/dorsal direction so that the cross beam 5 extends from ventral to dorsal at an angle of about 17° relative to the horizontal. This inclination which may be between 15° and 20° relative to a horizontal plane serves as protection for an undesired sliding out of the anchoring part after being driven into a tibia at 11 (see FIGS. 4 and 5).

Referring to FIGS. 4 and 5, in order to implant the anchoring part, the tibia is surgically prepared. For example, as indicated in FIG. 5, a condyle is removed to provide a generally flat surface for receiving the bearing element 1 of the anchoring part. Thereafter, the anchoring part can be inserted, for example by hammering in a direction parallel to the enlargement or cross beam 5, so that the blade like stem 6 penetrates into the tibia head 11 from ventral to dorsal, i.e. from left to right in FIG. 4. At this time, the cutting edge 8 at the dorsal edge penetrates into the bone. At the same time, the cutting edge 9 on the cross beam 5 cuts into the bone and compacts the bone tissue upwardly, as viewed in FIG. 4.

As indicated in FIG. 4, the bearing element 1 may also be inclined relative to the axis 12 of the tibia by a few degrees, for example up to 5°. Although this inclination may not be necessary, the inclination causes the resultant load to have a slight horizontal force component in the dorsal direction so as to additionally increase the protection against the anchoring part sliding out of the tibia bone 11.

Referring to FIGS. 6 to 10, the enlargement 5 may be of other suitable shapes than a flat web. For example, the enlargement may be of V-shaped cross-section (FIG. 6), circular cross-section (FIG. 7), semi-circular cross-section (FIG. 8) or J-shaped cross-section (FIGS. 9 and 10).

The invention thus provides a metal tibial anchoring part which can be readily inserted into a tibia bone for a partial knee joint prosthesis without interference with the ligament arrangement of the natural knee joint.

The anchoring part is such as to be fixable on the tibia head from ventral to dorsal without requiring manipulations at the tibia in the direction of the longitudinal axis of the tibia. Thus, it is not necessary to proceed with any ligament detachments during a surgical procedure.

What is claimed is:

1. A metal tibial anchoring part for a partial knee joint prosthesis, said part comprising
    a flat semicircular bearing element defining a tibial plateau for receiving a plastic bearing element for a femur condyle; and
    a fixing element secured to and extend from said bearing element, said fixing element having a lower edge sloping in a downward direction from ventral to dorsal in a distal direction and having a cutting edge along a dorsal front edge.

2. An anchoring part as set forth in claim 1 wherein said fixing element has a blade-like stem extending perpendicularly from said bearing element and an enlargement at a distal end of said stem.

3. An anchoring part as set forth in claim 2 wherein said stem and enlargement of said fixing element define a T-shaped cross-section.

4. An anchoring part as set forth in claim 3 wherein said stem has a pair of side walls defining said cutting edge centrally thereof and said enlargement has a one-sided cutting edge sharpened to distal.

5. An anchoring part as set forth in claim 1 wherein said fixing element has openings therein for ingrowth of bone tissue.

6. An anchoring part as set forth in claim 1 wherein said fixing element has a dorsal edge and a ventral edge, each said edge being inclined to ventral.

7. A metal tibial anchoring part for a partial knee joint prosthesis, said part including
    a semi-circular bearing element defining a tibial plateau for receiving a bearing element for a femur condyle; and
    a blade-like fixing element extending perpendicularly from said bearing element and having a cutting edge at a dorsal edge for penetrating into a tibia.

8. An anchoring part as set forth in claim 7 wherein said fixing element has a pair of side walls defining said cutting edge centrally thereof.

9. An anchoring part as set forth in claim 7 wherein said fixing element has openings therein for ingrowth of tissue.

10. An anchoring part as set forth in claim 7 wherein said fixing element has an enlargement along a distal edge thereof, said distal edge being inclined relative to said tibial plateau.

11. An anchoring part as set forth in claim 10 wherein said enlargement has a cutting edge along a dorsal edge thereof.

12. An anchoring part as set forth in claim 10 wherein said enlargement is a flat web.

13. An anchoring part as set forth in claim 10 wherein said enlargement is of V-shaped cross-section.

14. An anchoring part as set forth in claim 10 wherein said enlargement is of circular cross-section.

15. An anchoring part as set forth in claim 10 wherein said enlargement is of semi-circular cross-section.

16. An anchoring part as set forth in claim 10 wherein said enlargement is of J-shaped cross-section.

17. An anchoring part as set forth in claim 10 wherein said bearing element is flat.

18. A metal tibial anchoring part for a partial knee joint prosthesis, said part comprising
    a flat semicircular bearing element defining a tibial plateau for receiving a plastic bearing element for a femur condyle; and
    a fixing element secured to and extending perpendicularly from said bearing element, said fixing element having a distal edge sloping at an angle relative to said tibial plateau and having a cutting edge along a dorsal front edge.

19. An anchoring part as set forth in claim 18 wherein said fixing element has an enlargement at said distal edge.

20. An anchoring part as set forth in claim 19 wherein said enlargement is inclined at an angle of between 15° and 20° relative to said tibial plateau.

* * * * *

UNITED STATES PATENT AND TRADEMARK OFFICE
CERTIFICATE OF CORRECTION

PATENT NO. : 4,963,153

DATED : October 16, 1990

INVENTOR(S) : BRUNO NOESBERGER, et al

It is certified that error appears in the above-identified patent and that said Letters Patent is hereby corrected as shown below:

```
Column 2, line 23 change "faCe" to -face-
Column 2, line 25 change "kno Wn" to -known-
Column 2, line 65 change "In the" to -In addition, the-
```

Signed and Sealed this

Second Day of June, 1992

*Attest:*

DOUGLAS B. COMER

*Attesting Officer*     *Acting Commissioner of Patents and Trademarks*